US012582441B2

(12) United States Patent　　　　　(10) Patent No.:　US 12,582,441 B2

Azmi　　　　　　　　　　　　　　　(45) Date of Patent:　　Mar. 24, 2026

(54) WIRE LEAD ANCHORING DEVICE

(71) Applicant: Hooman Azmi, Cresskill, NJ (US)

(72) Inventor:　Hooman Azmi, Cresskill, NJ (US)

( * ) Notice:　Subject to any disclaimer, the term of this patent is extended or adjusted under 35 U.S.C. 154(b) by 130 days.

(21) Appl. No.: 18/605,905

(22) Filed:　Mar. 15, 2024

(65)　　　　　Prior Publication Data

US 2024/0315730 A1　　Sep. 26, 2024

Related U.S. Application Data

(60) Provisional application No. 63/453,778, filed on Mar. 22, 2023.

(51) Int. Cl.
*A61B 17/34*　　　　(2006.01)
(52) U.S. Cl.
CPC ................................. *A61B 17/3468* (2013.01)
(58) Field of Classification Search
CPC ... A61B 17/122; A61B 17/08; A61B 17/3468; A61B 90/11; A61B 2017/347; A61B 90/10; A61B 2090/103; A61B 17/0401; A61B 17/0487; A61N 1/0539; A61N 1/0558; A61N 1/05; A61N 1/0529; A61N 1/0534; A61N 1/0531; A61N 1/057; A61N 1/37518; A61M 2025/024; A61M 25/02
See application file for complete search history.

(56)　　　　　References Cited

U.S. PATENT DOCUMENTS

| | | | |
|---|---|---|---|
| 2005/0038453 A1* | 2/2005 | Raulerson | A61M 25/02 |
| | | | 606/151 |
| 2011/0238113 A1 | 9/2011 | Fanton et al. | |
| 2015/0018916 A1 | 1/2015 | Leven | |
| 2023/0191118 A1* | 6/2023 | Sochor | A61N 1/0539 |
| | | | 607/116 |

FOREIGN PATENT DOCUMENTS

| | | |
|---|---|---|
| CN | 11546193512/2022 | 12/2022 |
| WO | WO | 6/2012 |
| | 2012/07945006/2012 | |

OTHER PUBLICATIONS

International Search Report & Written Opinion For Application PCT/US2024/020046 Dated: Sep. 5, 2024.

* cited by examiner

*Primary Examiner* — Katherine M Shi

(74) *Attorney, Agent, or Firm* — Neil D. Gershon

(57)　　　　　ABSTRACT

An anchoring device that is configured to receive a wire lead during a surgical procedure and which includes an anchor and a frame. The anchor defines a longitudinal axis and is configured for insertion into an access site in a patient. The anchor includes a first body portion and a second body portion that is pivotably connected to the first body portion such that the anchoring device is reconfigurable between an open configuration and a closed configuration. The frame is connected to the anchor and is configured to facilitate reconfiguration of the anchoring device between the open configuration and the closed configuration.

18 Claims, 8 Drawing Sheets

WIRE LEAD ANCHORING DEVICE

CROSS-REFERENCE TO RELATED APPLICATION(S)

This application claims the benefit of and priority to U.S. Provisional Application No. 63/453,778 filed on Mar. 22, 2023, the entire contents of which is hereby incorporated by reference.

TECHNICAL FIELD

This application is directed to a device for securing wire leads within a patient and, more specifically, to a wire lead anchoring device that is configured for insertion into an access site in a patient's tissue (e.g., a burr hole in a patient's skull).

BACKGROUND

Some surgical (e.g., neurological) procedures require the placement of wire leads at a target site within a patient's brain, which typically include a series of anchors that are configured to engage the patient's tissue and thereby secure the wire leads. These wire leads are used to deliver therapeutic electrical stimulation (electrical impulses to the targeted brain area) or record brain activity for diagnosis and monitoring various neurological conditions.

Ensuring proper anchoring and fixation of these wire leads is critical for their effective and safe function in clinical applications. Known wire leads can sometimes be subject to inadvertent dislodgement or other such unintended movement over a period of time. Such inadequate securement of wire leads within the skull can result in disadvantages and complications. Improper anchoring may lead to suboptimal positioning of electrodes, compromising the accuracy and efficacy of therapeutics, e.g., inadequate stimulation of target brain regions, diminishing the therapeutic benefits. Inadequate anchoring of wire leads within the skull may increase the risk of tissue irritation or inflammation at the implantation site and cause unwanted movement within the brain tissue causing undesired side effects. Further, movement of the wire lead could lead to unwanted gaps between the wire lead and the skull, posing a risk of infection. Additionally, if such movement or displacement causes sufficient mechanical stress on the leads, it can result in wire breakage or disconnection, thereby interrupting the delivery of electrical impulses or recording of brain activity. Such displacement can therefore compromise the reliability and effectiveness of the wire lead.

Therefore, the need exists to improve the securement of wire leads during a surgical procedure to ensure proper functioning of the leads over a period of time and prevent complications that can occur if movement is not restricted.

SUMMARY

The present invention overcomes the problems and deficiencies of the prior art by providing a device that improves the securement of wire leads during a surgical procedure. In short, the device includes a first component configured to encapsulate the lead and a second component to facilitate movement of the first component and facilitate anchoring the device to the patient's skull. The device of the present invention limits, and in some cases, fully restricts, movement of the wire lead to avoid the risks, potential complications and compromised clinical efficacy associated with unwanted wire movement.

In one aspect of the present invention, an anchoring device is provided that is configured to receive one (or in some embodiments, multiple) wire leads during a surgical procedure and which includes an anchor and a frame. The anchor defines a longitudinal axis and is configured for insertion into an access site in a patient tissue. The anchor includes a first body portion and a second body portion that is movably (e.g., pivotably) connected to the first body portion such that the anchoring device is reconfigurable between an open configuration and a closed configuration. The frame is connected to the anchor and is configured to facilitate reconfiguration of the anchoring device between the open configuration and the closed configuration.

In some embodiments, the first body portion and the second body portion may be connected by a hinge portion that extends in generally parallel relation to the longitudinal axis. In some embodiments, the frame may include a first frame portion that is connected to the first body portion and a second frame portion that is connected to the second body portion.

In some embodiments, the first frame portion may be pivotable in relation to the first body portion, and the second frame portion may be pivotable in relation to the second body portion.

In some embodiments, the frame may include one or more latches that are configured to lock the anchoring device in the closed configuration. The latches may include recesses that are configured to receive one or more wire leads to guide the one or more wire leads away from the patient.

In some embodiments, the anchoring device may further include a cap that is configured for engagement with the anchor to further secure the anchoring device within the access site. The cap may include a resilient material such that, upon connection of the cap to the anchor, biasing forces are generated that are directed radially outward. This can help further secure the anchor. In some embodiments, the cap may include a first leg that is configured for insertion into the first body portion and a second leg that is configured for insertion into the second body portion such that, upon connection of the cap to the anchor, the first leg extends into the first body portion and the second leg extends into the second body portion. In some embodiments, the first leg and the second leg may extend in non-parallel relation to the longitudinal axis.

In another aspect of the present invention, an anchoring device is provided that is configured to receive a wire lead during a surgical procedure and which includes an anchor and a frame. The anchor defines a longitudinal axis and is configured for insertion into a burr hole in a patient's skull. The anchor includes first and second body portions, each of which preferably includes a generally (substantially) C-shaped configuration that defines inner walls. The first and second body portions are configured for relative movement such that the anchoring device is reconfigurable between an open configuration, in which the inner walls of the first and second body portions are separated, and a closed configuration, in which the inner walls of the first and second body portions are positioned in adjacent relation such that the first and second body portions collectively define a passageway configured to receive the wire lead. The frame is connected to the anchor and is configured to facilitate reconfiguration of the anchoring device between the open configuration and the closed configuration.

In some embodiments, the anchor may include a depression that is in communication with the passageway and which is configured to receive the wire lead to inhibit excess force from being applied thereto. In some embodiments, the depression may be located at an end of the anchor.

In some embodiments, the frame may be pivotable in relation to the anchor about a pivot axis that extends in generally orthogonal relation to the longitudinal axis.

In some embodiments, the frame may include one or more latches that are configured to lock the anchoring device in the closed configuration, wherein the one or more latches can extend transversely across the anchoring device in generally orthogonal relation to the longitudinal axis.

In another aspect of the present invention, a method of performing a surgical procedure is provides that includes: positioning a wire lead between first and second body portions of an anchoring device; reconfiguring the anchoring device from an open configuration into a closed configuration to thereby retain the wire lead within the anchoring device; locking the anchoring device in the closed configuration; and inserting the anchoring device into the access site.

In some embodiments, reconfiguring the anchoring device from the open configuration into the closed configuration may include pivoting the first and second body portions about a hinge portion.

In some embodiments, the method may further include connecting a cap to the anchoring device to further secure the anchoring device within the access site. In some embodiments, connecting the cap to the anchoring device may include connecting the cap to the anchoring device such that the wire lead extends through the cap. In some embodiments, connecting the cap to the anchoring device may include inserting legs on the cap into openings in the first and second body portions to thereby bias the first and second body portions radially outward.

BRIEF DESCRIPTION OF THE DRAWINGS

So that those having ordinary skill in the art to which the subject disclosure pertains will more readily understand how to make and use the wire lead anchoring device disclosed herein, as well as the various components thereof, some embodiments will be described in detail hereinbelow with reference to the drawings, which are intended to be viewed in conjunction with the detailed description that follows. According to common practice, the drawings may not be to-scale, and the dimensions illustrated may be arbitrarily expanded or reduced. Additionally, some components, elements, and/or features may be omitted from some drawings (e.g., in the interest of clarity).

4

Figures 5, 6:
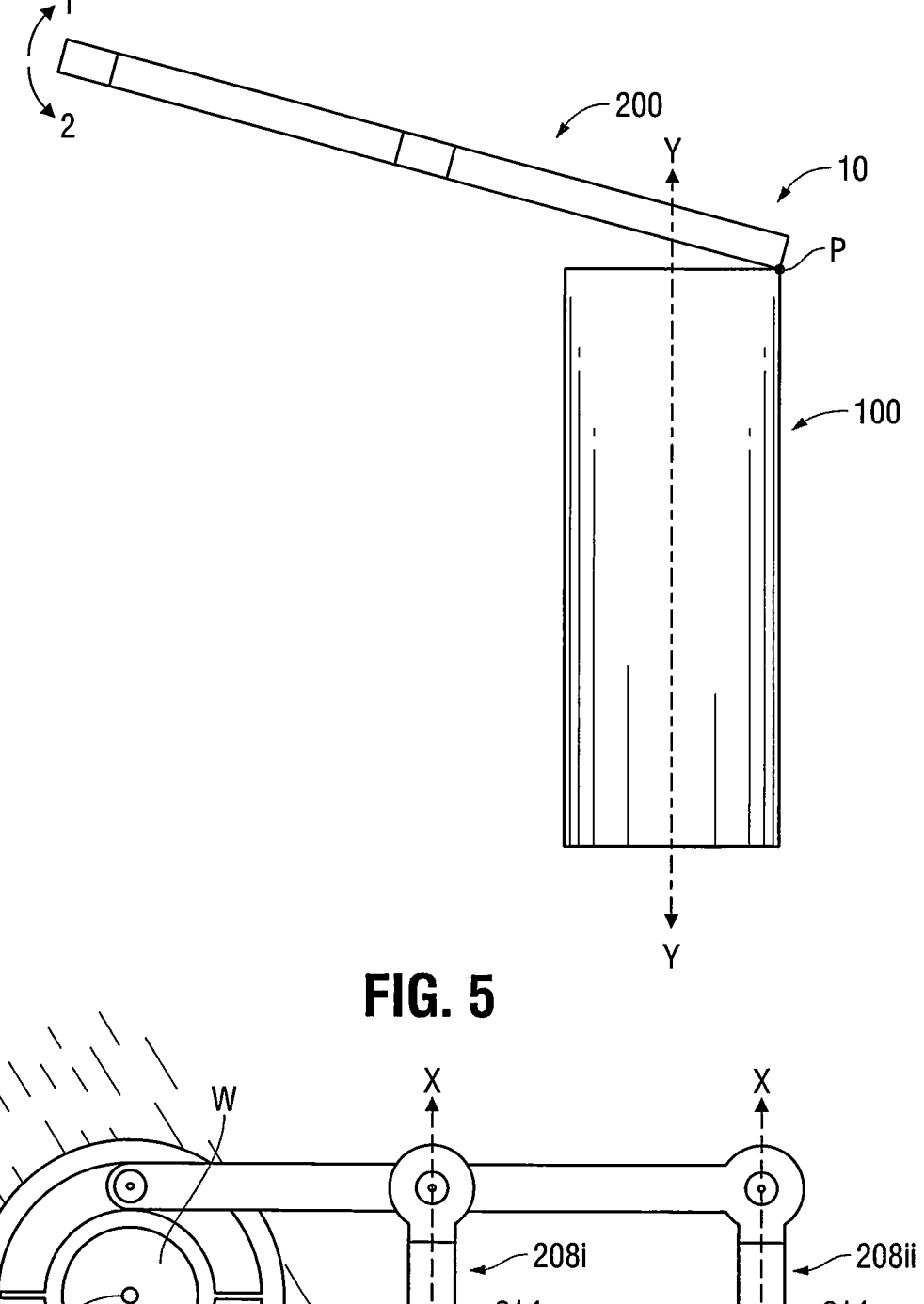
FIG. 5 is a side plan view of an alternate embodiment of the anchoring device of FIG. 1.
FIG. 6 is a top plan view of an alternate embodiment of the anchoring device of FIG. 1.
Figure 7:
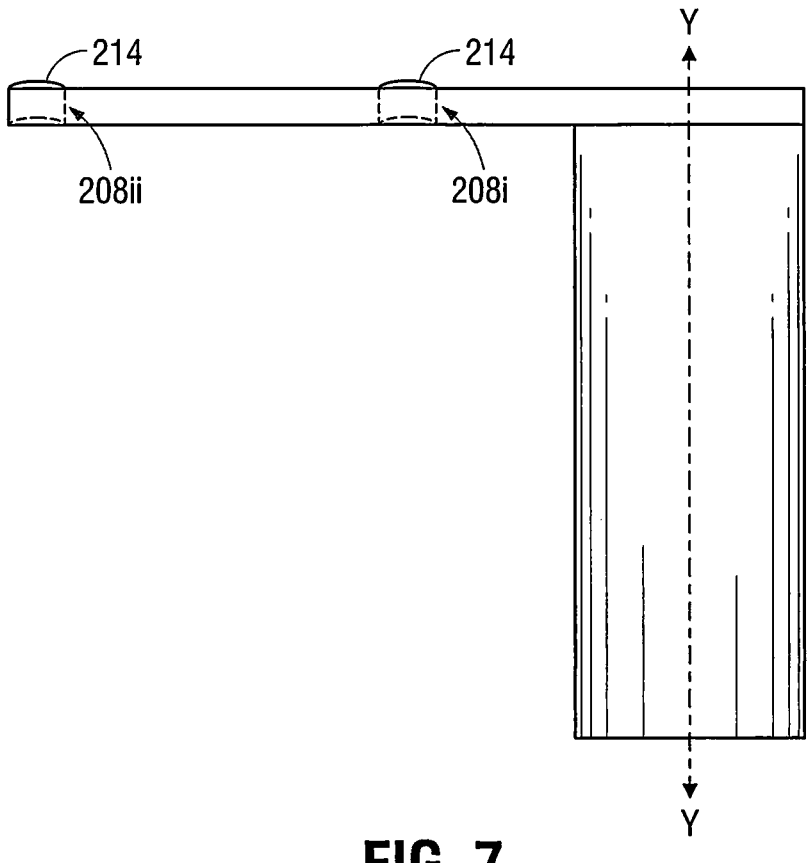

FIG. 7 is a side plan view of the anchoring device shown in FIG. 6.

Figure 1:
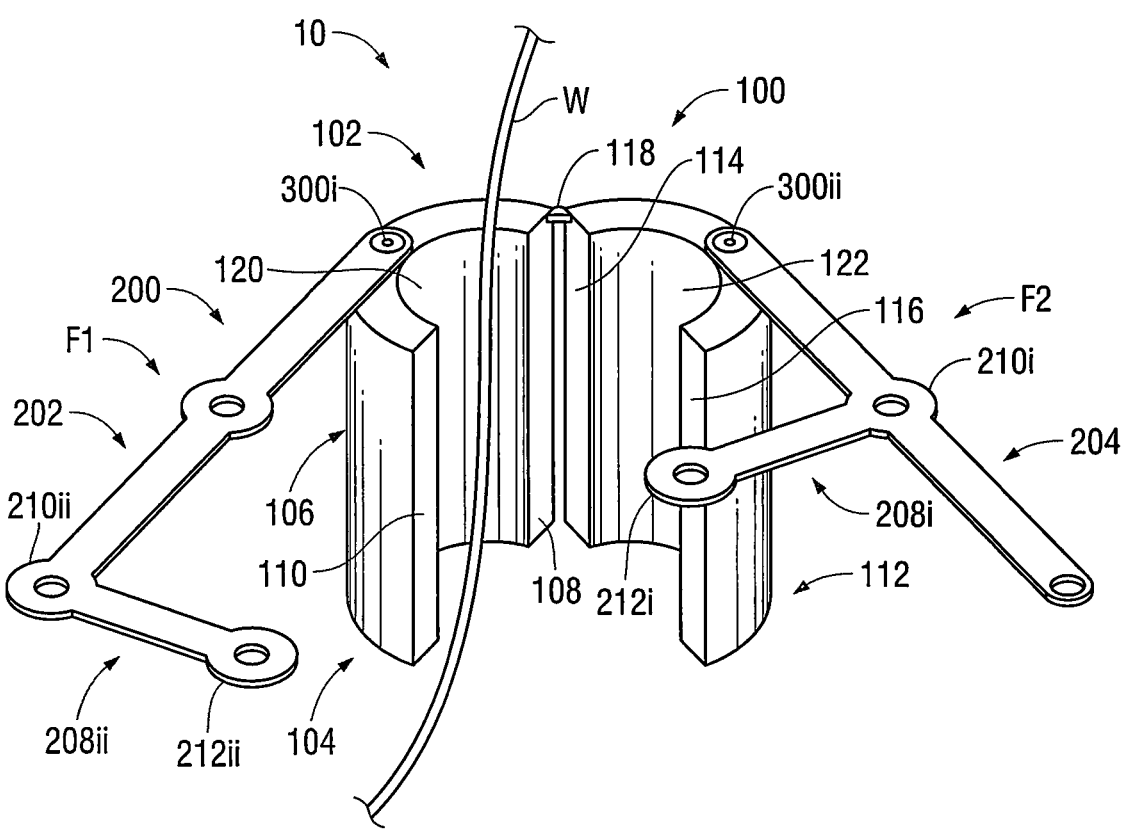
FIG. 1 is a top perspective view of an anchoring device according to one embodiment of the present invention, which includes an anchor and a frame, shown in an open configuration (condition/position).
Figure 8:
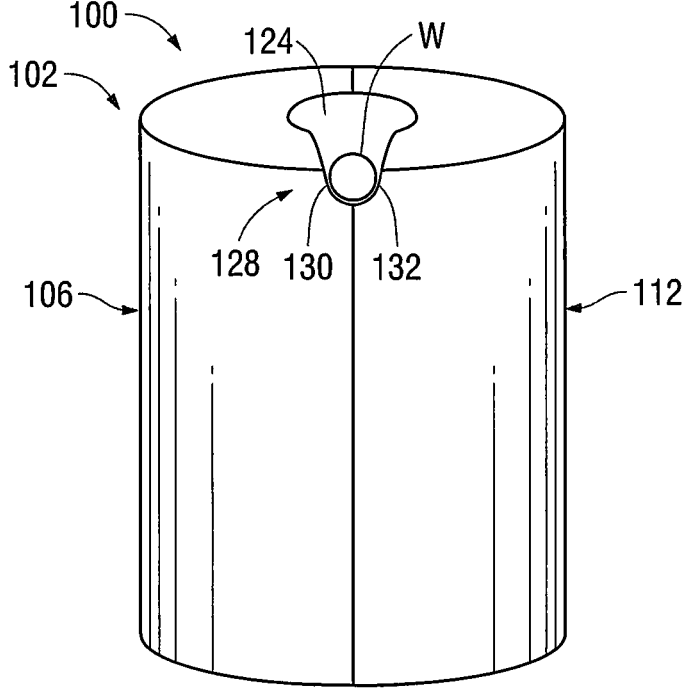

FIG. 8 is a top perspective view of an alternate embodiment of the anchor of FIG. 1.

Figure 9:
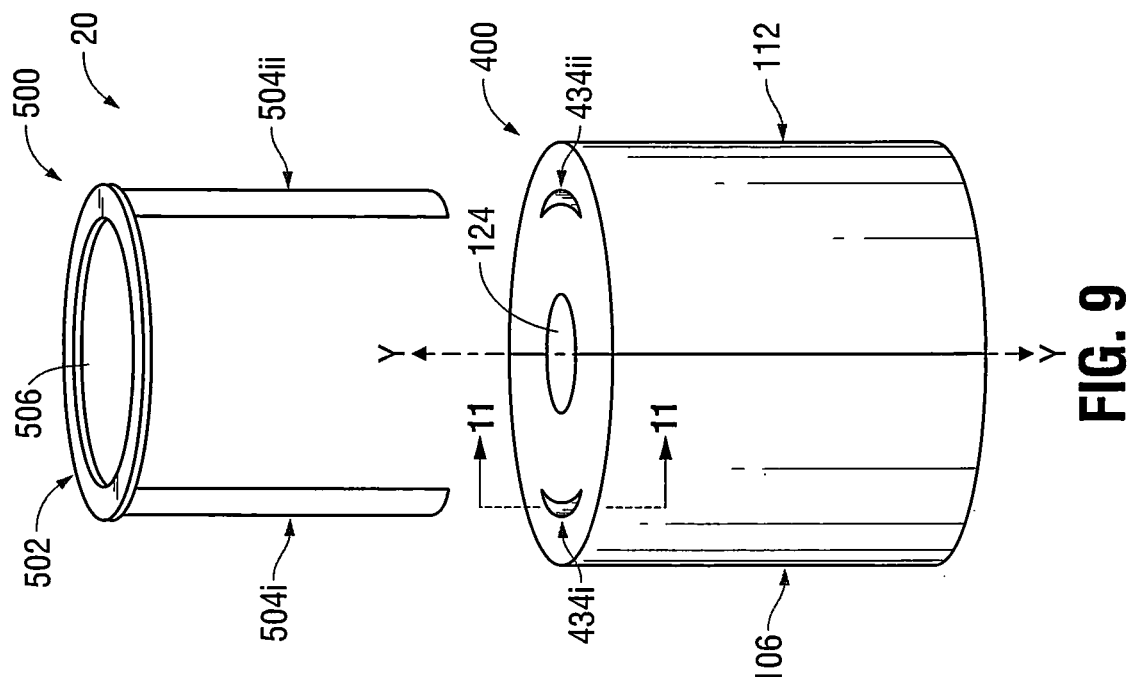

FIG. 9 is a partial, top, perspective view of an alternate embodiment of the anchoring device shown in FIG. 1, which includes an alternate embodiment of the anchor and a cap, shown with parts separated.

Figure 10:
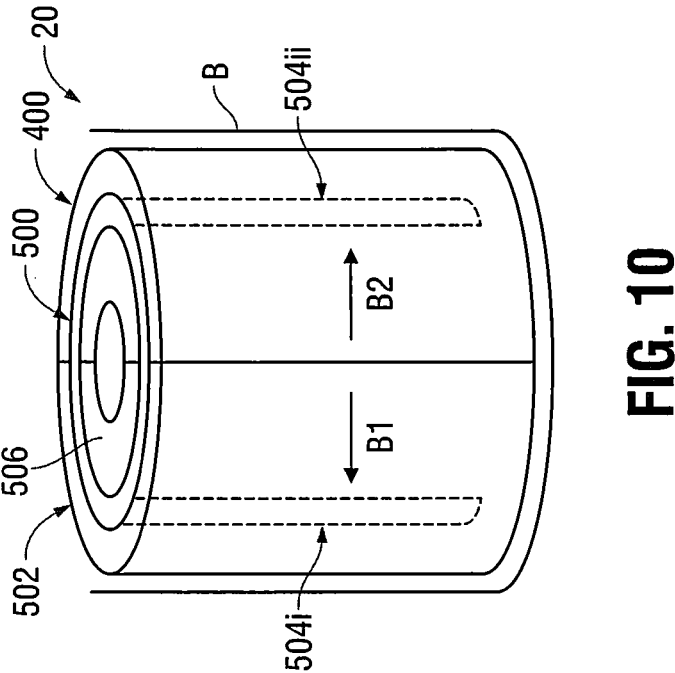

FIG. 10 is a partial, top, perspective view of the anchoring device of FIG. 9 shown upon assembly.

Figure 11:
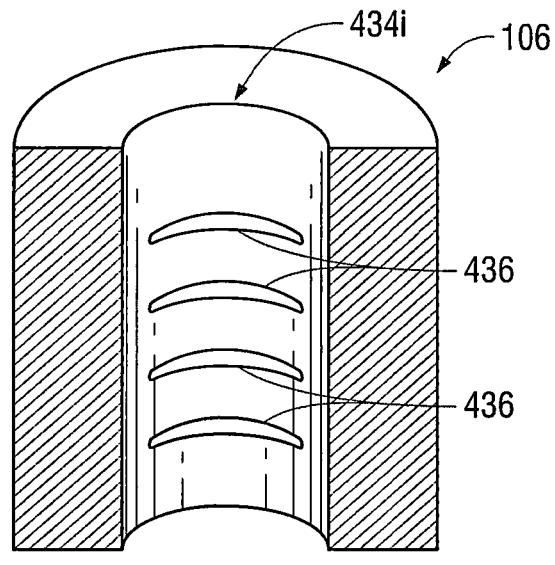

FIG. 11 is a cross-sectional view taken along line 11-11 in FIG. 9 showing projections on the inner wall of the opening.

Figure 12:
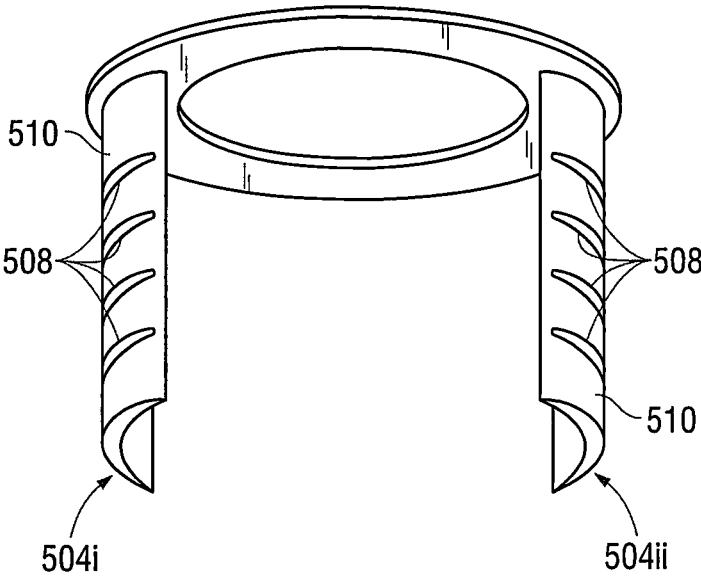

FIG. 12 is a bottom, perspective view of an alternate embodiment of the cap shown in FIG. 9.

Figure 13:
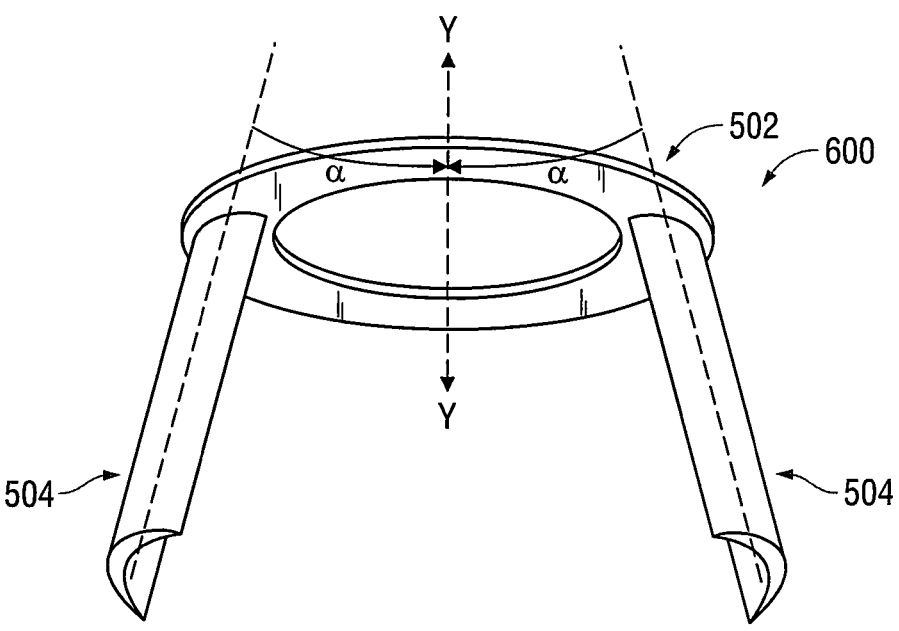

FIG. 13 is a bottom, perspective view of an alternate embodiment of the cap shown in FIG. 9.

Figure 14:
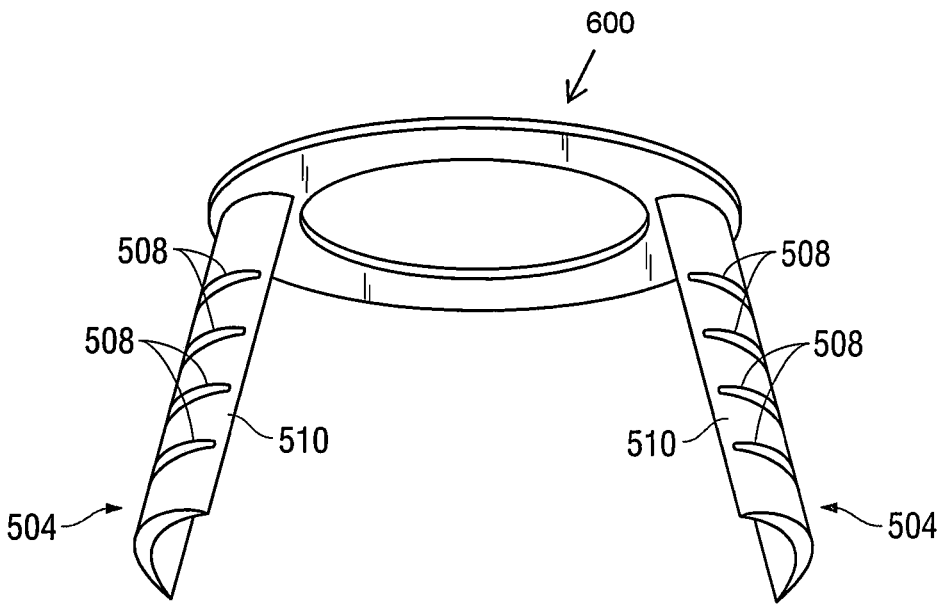

FIG. 14 is a bottom, perspective view of an alternate embodiment of the cap shown in FIG. 13.

DETAILED DESCRIPTION

The present invention provides an anchoring device that is configured to receive, guide, and protect one or more wire leads (e.g., a single wire lead or multiple wire leads) during a surgical procedure. More specifically, the anchoring device described herein includes an anchor that is configured for insertion into an access site in a patient's tissue (e.g., a burr hole in a patient's skull) and a frame that is connected to the anchor, with the purpose of further securing the wire. The anchor in preferable embodiments includes body portions that are pivotably connected together, which allows for reconfiguration of the anchoring device between open and closed configurations via manual manipulation of the frame. The anchoring of the device restricts (and in some embodiments limits) movement of the wire lead, keeping it secure over a period of time and avoiding the pitfalls and disadvantages of wire movement described above.

In addition, the wire anchoring device provides a low profile, thereby being cosmetically more acceptable and also more appropriate for patients who may have thin scalps, preventing further risk of skin erosion over the device.

Referring now to the drawings and particular embodiments of the present disclosure, like reference numerals identify similar structural features of the devices/system throughout the several views. With initial reference to FIGS. 1-4, the anchoring device of the present invention is illustrated, and designated generally by the reference numeral 10. The anchoring device 10 is configured for insertion into an access site A (FIG. 2) in a patient's tissue T (e.g., a burr hole B in a patient's skull S) in order to secure one or more wire leads W and includes an anchor 100 and a frame 200. It is envisioned that the anchoring device 10 (e.g., the anchor 100 and the frame 200) may include (e.g., may be formed from) any suitable biocompatible material or combination of materials (either metallic or non-metallic).

Figure 2:
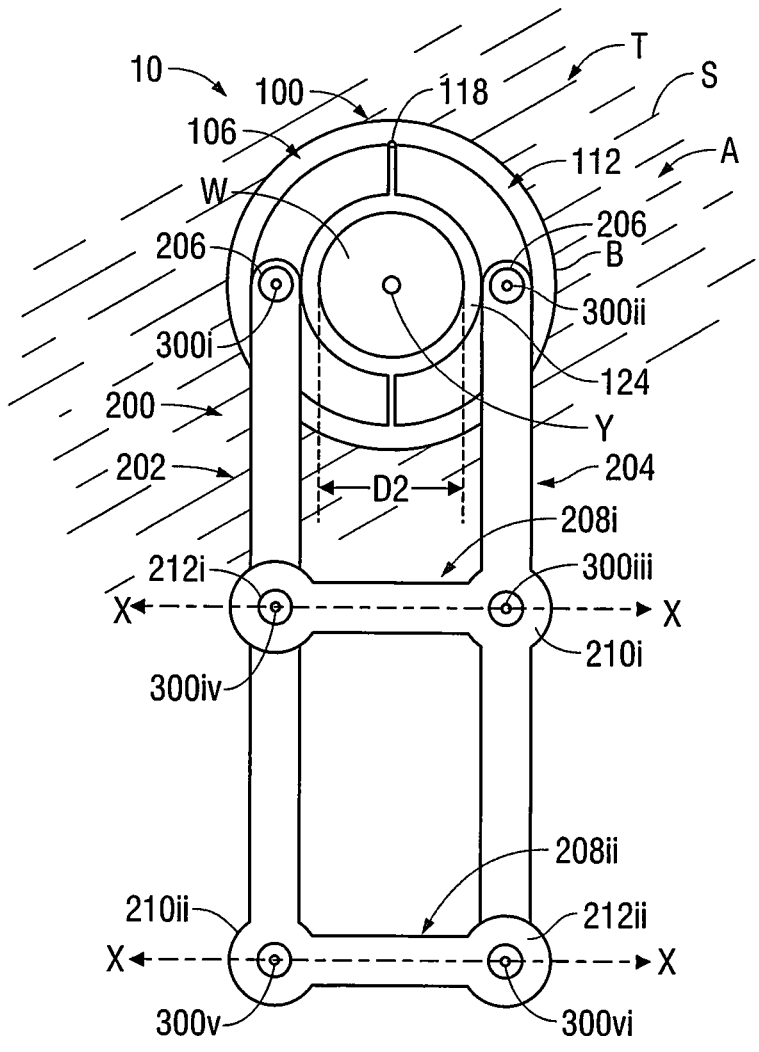
FIG. 2 is a top plan view of the anchoring device of FIG. 1 shown in a closed configuration and positioned within an access site in a patient.
Figure 3:
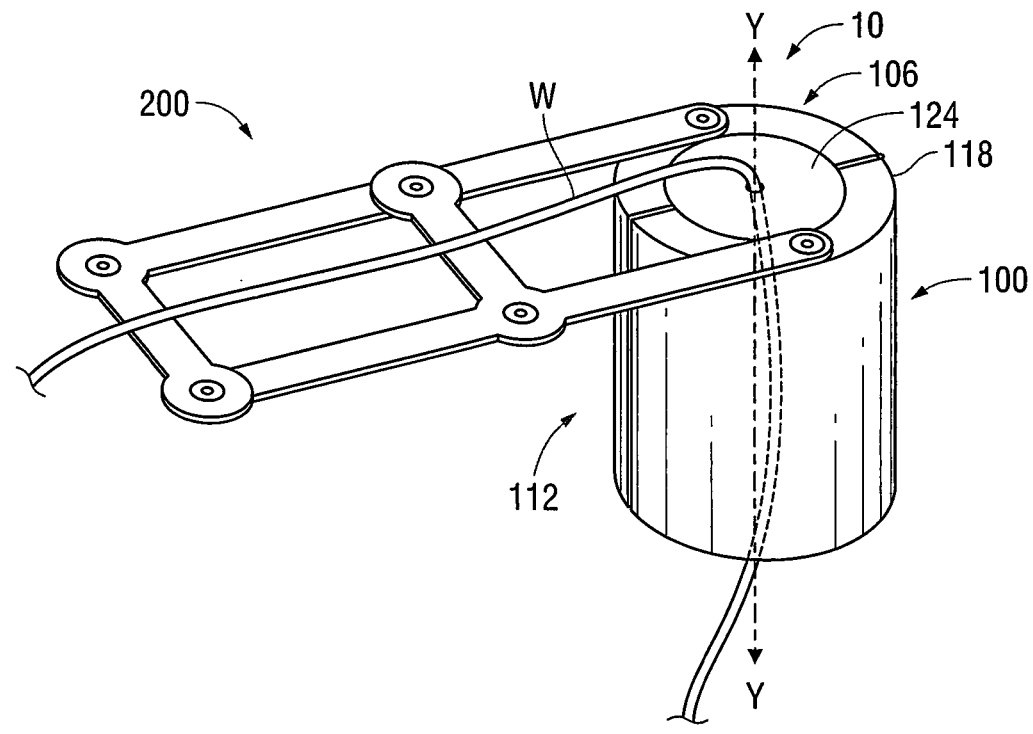
FIG. 3 is a top perspective view of the anchoring device of FIG. 1 shown in the closed configuration (condition/position).

The anchor 100 is generally cylindrical (tubular) in configuration and defines opposite outer (first) and inner (second) ends 102, 104, respectively, and a longitudinal axis Y (FIGS. 2, 3). The anchor 100 includes a first body portion 106 defining inner walls 108, 110 (FIG. 1), and a second body portion 112 defining inner walls 114, 116. The body portions 106, 112 are configured for relative movement such that the anchoring device 10 is reconfigurable between an open configuration (condition/position) (FIG. 1), in which the inner walls 108, 110 of the body portion 106 are separated from the inner walls 114, 116 of the body portion 112, and a closed configuration (condition/position) (FIGS.

2-4), in which the inner walls 108, 110 of the body portion 106 are positioned adjacent to (e.g., are in engagement (contact) with) the inner walls 114, 116 of the body portion 112, respectively. More specifically, the body portions 106, 112 are pivotably connected via a hinge portion 118, which extends in generally parallel relation to the longitudinal axis Y. Other ways to connect the two body portions 106, 112 are also contemplated and are not limited to hinged or pivotal connection.

Figure 4:
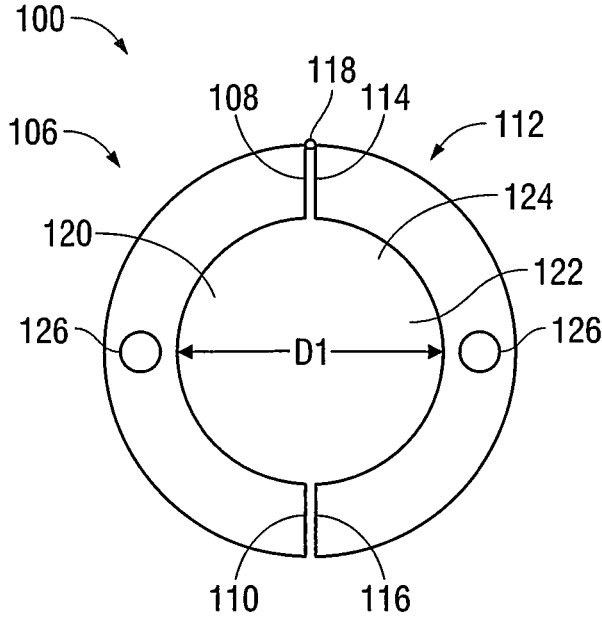
FIG. 4 is a top plan view of the anchor shown in FIG. 1.

As seen in FIGS. 1 and 4, the body portions 106, 112 each include a generally C-shaped transverse cross-sectional configuration and define respective channels 120, 122. Upon closure of the anchor 100, the body portions 106, 112 collectively define a central passageway 124 that extends through the anchor 100. The passageway 124, formed by channels 120, 122, defines a generally annular transverse cross-sectional configuration and extends in (generally) parallel relation to the longitudinal axis Y. As described in further detail below, during use of the anchoring device 10, the passageway 124 receives (and guides) the wire lead(s) W such that the wire lead(s) W extends from the target site within the patient, through the access site A (e.g., the burr hole B) via the anchoring device 10 (e.g., the anchor 100), to a location external of the patient.

The passageway 124 formed by the two body portions 106, 112, defines an inner transverse cross-sectional dimension D1 (FIG. 4) (e.g., a diameter) that exceeds, but closely approximates, an outer transverse cross-sectional dimension D2 (e.g., a diameter) defined by the wire lead(s) W. For example, it is envisioned that that the inner transverse cross-sectional dimension D1 of the passageway 124 may exceed the outer transverse cross-sectional dimension D2 of the wire lead by about 5% to about 10%, although other dimensions are also contemplated. It should be appreciated, however, that the specific configuration (e.g., cylindrical with circular cross-sectional passageway) and dimension of the anchoring device 10 (e.g., the inner transverse cross-sectional dimension D1 of the passageway 124) may be varied in alternate embodiments (e.g., depending upon the configuration of the wire lead(s) W, the specific surgical procedure being performed, etc.) without departing from the scope of the present invention. As such, embodiments of the anchor 100 in which the passageway 124 may define both larger and smaller inner transverse cross-sectional dimensions D1 are also envisioned herein.

The frame 200 is connected to the anchor 100 and is configured to facilitate the manual application of force thereto in order to open and close the anchor 100 during reconfiguration of the anchoring device 10 between the open configuration (condition/position) and the closed configuration (condition/position). More specifically, the frame 200 includes first and second frame portions 202, 204 that are respectively connected to the body portions 106, 112 of the anchor 100 (e.g., at the outer end 102 thereof). More specifically, the body portions 106, 112 and the frame portions 202, 204 include (define) respective corresponding apertures 126 (FIG. 4), 206 (FIG. 2) that are configured to receive fasteners 300i, 300ii (e.g., bolts, screws, rivets, pins, etc.) to thereby mechanically connect the frame 200 and the anchor 100 together. In addition, frame 200 will overly the wire and help anchor it in its position to the skull.

In the illustrated embodiment, the anchor 100 and the frame 200 are configured such that the fastener 300i fixedly (e.g., non-movably) connects the frame portion 202 to the body portion 106, and the fastener 300ii fixedly (e.g., non-movably) connects the frame portion 204 to the body portion 112. Alternatively, however, it is envisioned that the frame portions 202, 204 may be movably (e.g., pivotably) connected to the body portions 106, 112, respectively, such that the frame 200 is pivotable in relation to the anchor 100 about a pivot axis P (FIG. 5) that extends in (generally) orthogonal relation to the longitudinal axis Y. Pivotably connecting the frame portions 202, 204 to the respective body portions 106, 112 facilitates articulation of the frame 200 in relation to the anchor 100 in the directions identified by arrows 1 and 2 (FIG. 5), which allows for increased control of the anchoring device 10 during placement, use, and/or removal. Also envisioned is an embodiment wherein frame 200 and 204 are hinged to body portions (parts) 106 and 112.

In order to secure the frame portions 202, 204 together and thereby stabilize and lock the anchoring device 10 in the closed configuration, e.g., prior to insertion of the anchor 100 into the burr hole B (FIG. 2), in some embodiments, such as that illustrated in FIGS. 1-5, the frame 200 includes one or more latches (locking members) 208.

Each latch 208 extends transversely across the anchoring device 10 along a corresponding axis X (FIG. 2) that is preferably oriented in generally orthogonal relation to the longitudinal axis Y. In the illustrated embodiment, the anchoring device 10 includes two latches 208i, 208ii. It should be appreciated, however, the particular number of latches 208 may be increased or decreased in various embodiments without departing from the scope of the present invention (e.g., depending upon the configuration of the wire lead(s) W, the specific configuration of the anchoring device 10, the specific surgical procedure being performed, etc.). As such, embodiments of the anchoring device 10 including both fewer and greater numbers of latches 208 are envisioned herein, as are embodiments of the anchoring device 10 that are devoid of the latch(es) 208. It is also envisioned that the latches may have allowance for a conduit which will overly the wire to secure it further.

The latches 208 each include opposite (first and second) ends 210, 212 and are connected to (engaged with) the frame portions 202, 204. More specifically, in the illustrated embodiment, the latch 208i includes a first end 210i that is connected to (engaged with) the frame portion 204 by a fastener 300iii and a free second end 212i that is configured for engagement with (connection to) the frame portion 202 by a mechanical fastener 300iv, and the latch 208ii includes a first end 210ii that is connected to (engaged with) the frame portion 202 by a mechanical fastener 300v and a free second end 210ii that is configured for engagement with (connection to) the frame portion 204 by a mechanical fastener 300vi. Embodiments that are devoid of one or more of the fasteners 300iii-300vi are also envisioned herein and would not be beyond the scope of the present invention. For example, it is envisioned that the respective ends 210i, 210ii of the latches 208i, 208ii may be integrally (e.g., monolithically, unitarily) formed with the frame portions 204, 202 (e.g., such that the latches 208i, 208ii and the frame portions 202, 204 are formed from a single piece of material), and that the respective ends 212i, 212ii of the latches 208i, 208ii may be configured for mechanical engagement with the frame portions 202, 204 via the inclusion of corresponding engagement structures. Illustratively, it is envisioned that the respective ends 212i, 212ii of the latches 208i, 208ii may include detents that are configured for insertion into corresponding recesses defined by the frame portions 202, 204, or that the respective ends 212i, 212ii of the latches 208i, 208ii may include recesses that are configured to receive corresponding detents defined by the frame portions 202, 204.

In some embodiments, such as that illustrated in FIGS. 6 and 7, the latches 208 include recesses 214 that are configured to receive the wire lead(s) W in order to protect and guide the wire lead(s) W away from the patient by inhibiting (if not entirely preventing) the application of excess force thereto and, thus, bending, kinking, twisting, etc., of the wire lead(s) W. More specifically, the recesses 214 extend (vertically) into the latches 208 in (generally) orthogonal relation to the axes X and in (generally) parallel relation to the longitudinal axis Y defined by the anchor 100.

In some embodiments, such as that illustrated in FIG. 8, the anchor 100 may include a depression 128 at the end 102 thereof that is configured to receive the wire lead(s) W. The depression 128 is in communication with, and extends from, the passageway 124 so as to receive the wire lead(s) W as the wire lead(s) W exit the anchor 100 in order to further inhibit (if not entirely prevent) the application of excess force thereto and, thus, bending, kinking, twisting, etc., of the wire lead(s) W. More specifically, the depression 128 is collectively defined by a (first) indentation 130 included on the body portion 106 and by a (second) indentation 132 included on the body portion 112.

With reference again to FIGS. 1-4, use of the anchoring device 10 will be discussed during a surgical procedure in which one or more of the wire leads W are inserted into a patient in order to achieve a therapeutic effect. The wire lead can be used to deliver therapeutic electrical stimulation or record brain activity for diagnosis and monitor neurological conditions.

Initially, the wire lead(s) W is inserted through the access site A (FIG. 2) (e.g., the burr hole B) and are advanced to a target site (e.g., within the patient's skull S). Thereafter, with the anchoring device 10 in the open configuration (FIG. 1), the wire lead W is positioned between the body portions 106, 112 of the anchor 100 (e.g., within the channel 120 defined by the body portion 106 and/or within the channel 122 defined by the body portion 112). With the wire lead W in place, the anchoring device 10 is moved from the open configuration into the closed configuration (FIGS. 2-4) via the manual application of force to the frame portions 202, 204, which may be facilitated via pivoting of the frame 200 about the pivot axis P (FIG. 5). More specifically, inwardly directed forces F1, F2 (FIG. 1) are applied to the frame portions 202, 204, which are transmitted to the respective body portions 106, 112 via the connection established by the fasteners 300i, 300ii, respectively, or alternatively frame portions 202 and 204 are manufactured as part of body portions 106 and 112, and after body portions 106 and 112 are hinged close to secure the wire, frame portions 202 and 204 are hinged down over the wire to secure the wire further and also secure the overall construct to the skull. The body portions 106, 112 are thus caused to pivot about the hinge portion 118 until the inner walls 108, 110 of the body portion 106 are positioned adjacent to (e.g., are in engagement (contact) with) the inner walls 114, 116 of the body portion 112, respectively, whereby the wire lead W is retained within the passageway 124. Depending upon the particular configurations of the anchor 100 and the wire lead W (e.g., the specific dimensions D1 (FIG. 4), D2 (FIG. 2)), it is envisioned that closure of the anchoring device 10 may cause engagement of (contact between) the anchor 100 (e.g., the body portions 106, 112) and the wire lead W so as to inhibit (if not entirely prevent) relative movement therebetween. Alternatively, it is envisioned that the wire lead W may be freely movable within the passageway 124 upon closure of the anchoring device 10 (e.g., to allow for advancement, retraction, or other such repositioning of the wire lead W during the course of the surgical procedure).

Following closure of the anchor 100, the anchoring device 10 can be locked in the closed configuration via engagement of the latches 208i, 208ii with the respective frame portions 202, 204, (e.g., via insertion of the fasteners 300iii, 300iv, 300v, 300vi (FIG. 2) through the latches 208i, 208ii and into the frame portions 202, 204) or as discussed above, and the anchor 100 can be inserted into the access site A (FIG. 2) (e.g., the burr hole B).

In one method of use, the fasteners 300iii, 300iv, 300v, 300vi may be advanced through the frame 200 and into the patient's tissue (e.g., the patient's skull S (FIG. 2)) in order to further secure the anchor 100 within the burr hole B and thereby inhibit (if not entirely prevent) movement of the anchoring device 10 (and the wire lead(s) W) in relation to the patient. Alternatively, it is envisioned that one or more additional fasteners may be utilized in order to fix the anchoring device 10 in place. For example, it is envisioned that the additional fasteners(s) may be inserted and advanced through the anchor 100 (e.g., through the body portion 106 and/or the body portion 112) or through the frame 200 (e.g., through the frame portion 202 and/or the frame portion 204) and into the patient's tissue.

With reference now to FIGS. 9-11, another embodiment of the anchoring device 10 is illustrated, which is identified by the reference numeral 20. The anchoring device 20 is substantially similar in both structure and function to the anchoring device 10 discussed above (FIGS. 1-4) and, accordingly, will only be discussed with respect to any differences therefrom in the interest of brevity. As such, identical reference numerals will be utilized to refer to elements, structures, features, etc., common to the anchoring devices 10, 20.

In addition to the frame 200, which is omitted from FIGS. 9-11 in the interest of clarity, the anchoring device 20 includes an anchor 400 and a cap 500 that is configured for engagement with (connection to) the anchor 400 in order to further secure the anchoring device 20 within the burr hole B.

The anchor 400 is substantially similar to the aforedescribed anchor 100 (FIGS. 1-4) but has longitudinal openings 434 that extend into the body portions 106, 112 in (generally) parallel relation to the longitudinal axis Y. Alternatively, the openings 434 can be angled slightly inwardly toward the longitudinal axis. Although shown as including a pair of openings 434i, 434ii in the illustrated embodiment, it should be appreciated that the particular number of openings 434 may be increased without departing from the scope of the present invention (e.g., depending upon the configuration of the wire lead W (FIGS. 1-3), the specific surgical procedure being performed, etc.). As such, embodiments of the anchor 400 including three or more openings 434 are also envisioned herein.

The cap 500 includes a collar 502 and a pair of legs (fins) 504. The cap 500 defines a window or opening 506 that is configured to receive the wire lead(s) W such that the wire lead(s) W extends from the anchor 400 and through the collar 502 upon assembly of the anchoring device 20. In the illustrated embodiment, the collar 502 and the window 506 are each (generally) annular (e.g., circular) in configuration. It should be appreciated, however, that the specific configurations of the collar 502 and/or the window 506 may be altered in various embodiments without departing from the scope of the present disclosure (e.g., depending upon the configuration of the wire lead(s) W, the configuration of the anchor 400, etc.).

The legs 504 extend vertically from the collar 502 (downwardly in the orientation of FIG. 9) in (generally) parallel relation to the longitudinal axis Y and are configured for insertion into the openings 434 in the body portions 106, 112. Although shown as including a pair of legs 504*i*, 504*ii* in the illustrated embodiment, it should be appreciated that the particular number of legs 504 may be increased without departing from the scope of the present disclosure (e.g., depending upon the configuration of the anchor 400). As such, embodiments of the cap including three or more legs 504 are also envisioned herein. The openings 434 in the body portions would preferably correspond to the number of legs 504.

The cap 500 is composed of a resilient (flexible, deformable) material (either metallic or non-metallic) such that, upon connection of the cap 500 to the anchor 400 in the closed configuration (e.g., upon insertion of the legs 504 into the openings 434), biasing forces B1, B2 are generated via contact (engagement) between the cap 500 and the anchor 400, as seen in FIG. 10, which are directed radially outward and are transmitted to the body portions 106, 112 of the anchor 400 in order to further secure the anchor 400 and effectively lock the anchoring device 20 within the access site A (FIG. 2) (e.g., the burr hole B). The openings 434 and legs 504 can be for example configured so that when the legs are inserted, they press against the walls of the angled openings toward their normal parallel position to apply an outward force. In another example, projections on the wall of the openings could deflect the legs inwardly toward the passageway to generate outward biasing forces B1, B2.

In an alternate embodiment, the body portions 106, 112 include a plurality of projections (e.g., detents, ribs, etc.), which are located within the passageway 124. The projections are configured for engagement (contact) with the wire lead to enhance securement of the lead, e.g. can increase frictional engagement thereof. The projections 436 of FIG. 11 can be utilized in passageway 124.

Projections 436 (e.g., detents, ribs, etc.) could additionally or alternatively be provided within the openings 434 of the body portions 106, 112 which would provide an inwardly biasing force on legs 504 to bias the anchor halves inwardly to enhance gripping of the wire lead. Such projections 436 would be on the outer wall of openings 434*i*, 434*ii*.

Projections 436 could additionally or alternatively be provided within the openings 434 for engagement (contact) with the legs 504 to deflect the legs 504 outwardly which would result in enhancing the outwardly biasing forces directed outwardly to enhance securement of the anchor in the burr hole. Such projections would be on the inner wall of the openings 434*i*, 434*ii* (see FIG. 11).

As seen in FIG. 12, one or more projections 508 (e.g., detents, ribs, etc.) may also be included on exterior surfaces 510 of the legs 504, either in addition to, or instead of, the projections 436 included in the openings 434, to provide the inwardly biasing force or generate the outwardly biasing force.

FIG. 13 illustrates another embodiment of the cap 500, which is identified by the reference character 600. The cap 600 is substantially similar in both structure and function to the cap 500 discussed above (FIGS. 9-11) and, accordingly, will only be discussed with respect to any differences therefrom in the interest of brevity. As such, identical reference numerals will be utilized to refer to elements, structures, features, etc., common to the caps 500, 600.

In contrast to the cap 500, in which the legs 504 extend (vertically) from the collar 502 in (generally) parallel relation to the longitudinal axis Y, the legs 504 on the cap 600 extend from the collar 502 in non-parallel relation not the longitudinal axis Y such that each leg 504 subtends an (acute) angle $\alpha$ with the longitudinal axis Y. In the illustrated embodiment, the cap 600 is configured such that the angle $\alpha$ lies (substantially) within the range of (approximately) 5 degrees to (approximately) 45 degrees, although other ranges are also contemplated.

Due to the angled configuration of the legs 504, upon insertion into the openings 434 (FIG. 9), the legs 504 are deflected radially inward (e.g., towards the passageway 124), thereby generating the aforementioned biasing forces B1, B2 (FIG. 10). As such, varying the specific angle $\alpha$ at which the legs 504 extend in relation to the longitudinal axis Y allows for variation in the biasing forces B1, B2. More specifically, increasing the angle $\alpha$ results in the application of increased outward biasing forces B1, B2 to the body portions 106, 112 and, thus, the burr hole B, whereas decreasing the angle $\alpha$ results in the application of decreased biasing forces B1, B2.

In order to further increase the biasing forces B1, B2, in some embodiments, such as that illustrated in FIG. 14, it is envisioned that the cap 600 may also include the aforementioned projections 508 on the exterior surfaces 510 of the legs 504 and/or include projection in openings 434.

Although the systems, components, and methods described herein above relate to some embodiments of the disclosure, those skilled in the art will readily appreciate that changes and modifications may be made thereto without departing from the spirit and scope of the present invention as defined by the appended claims. Persons skilled in the art will understand that the various embodiments of the disclosure described herein and shown in the accompanying figures constitute non-limiting examples, and that additional components and features may be added to any of the embodiments discussed herein without departing from the scope of the present invention.

Note the device is configured to receive a single wire lead, but it is also contemplated it can receive (multiple) more than one wire lead.

It will be understood by those skilled in the art that the above particular embodiments are shown and described by way of illustration only. The principles and the features of the present disclosure may be employed in various and numerous embodiments thereof without departing from the scope and spirit of the invention as claimed. The above-described embodiments do not restrict the scope of the invention.

Additionally, persons skilled in the art will understand that the elements and features shown or described in connection with one embodiment may be combined with those of another embodiment without departing from the scope of the present invention.

Throughout the present disclosure, terms such as "approximately," "about", "generally," "substantially," and the like should be understood to allow for variations in any numerical range or concept with which they are associated and encompass variations on the order of 25% (e.g., to allow for manufacturing tolerances and/or deviations in design). For example, the term "generally parallel" should be understood as referring to configurations in which the pertinent components are oriented so as to define an angle therebetween that is equal to 180°±25% (e.g., an angle that lies within the range of (approximately) 135° to (approximately) 225°) and the term "generally orthogonal" should be understood as referring to configurations in with the pertinent components are oriented so as to define an angle therebetween that is equal to 90°±25% (e.g., an angle that lies within the range of (approximately) 67.5° to (approximately) 112.5°).

The recitation of numerical ranges by endpoints includes all numbers within the range.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. An anchoring device configured to receive a wire lead during a surgical procedure, the anchoring device comprising:
an anchor defining a longitudinal axis and configured for insertion into an access site in a patient, wherein the anchor includes:
a first body portion; and
a second body portion movably connected to the first body portion such that the anchoring device is reconfigurable between an open configuration and a closed configuration; and
a frame connected to the anchor and configured to facilitate reconfiguration of the anchoring device between the open configuration and the closed configuration,
wherein the frame includes a first frame portion connected to the first body portion and a second frame portion connected to the second body portion, the first frame portion is pivotable in relation to the first body portion, and the second frame portion is pivotable in relation to the second body portion.

2. The anchoring device of claim 1, wherein the first body portion and the second body portion are connected by a hinge portion extending in generally parallel relation to the longitudinal axis.

3. The anchoring device of claim 1, wherein the frame includes one or more latches configured to lock the anchoring device in the closed configuration.

4. The anchoring device of claim 3, wherein the one or more latches each include a recess configured to receive the wire lead to guide the wire lead away from the patient.

5. The anchoring device of claim 3, wherein the one or more latches extend transversely across the anchoring device in generally orthogonal relation to the longitudinal axis.

6. The anchoring device of claim 1, further comprising:
a cap configured for engagement with the anchor to further secure the anchoring device within the access site.

7. The anchoring device of claim 6, wherein the cap includes a resilient material such that, upon connection of the cap to the anchor, biasing forces are generated that are directed radially outward.

8. The anchoring device of claim 7, wherein the cap includes a first leg configured for insertion into the first body portion and a second leg configured for insertion into the second body portion such that, upon connection of the cap to the anchor, the first leg extends into the first body portion and the second leg extends into the second body portion.

9. The anchoring device of claim 8, wherein the first leg and the second leg extend in non-parallel relation to the longitudinal axis.

10. The anchoring device of claim 6, wherein engagement of the cap to the anchoring device includes inserting legs on the cap into openings in the first and second body portions to thereby bias the first and second body portions radially outward.

11. The anchoring device of claim 1, wherein
the access site is a burr hole in a skull of a patient, wherein the first and second body portions define inner walls, wherein in the open configuration, the inner walls of the first and second body portions are separated, and in the closed configuration, the inner walls of the first and second body portions are positioned in adjacent relation such that the first and second body portions collectively define a passageway configured to receive the wire lead.

12. The anchoring device of claim 11, wherein the first and second body portions are generally C-shaped in configuration.

13. The anchoring device of claim 1, wherein the anchoring device is locked in the closed position.

14. The anchoring device of claim 13, wherein the anchoring device is reconfigured from the open configuration into the closed configuration by pivoting the first and second body portions about a hinge portion.

15. An anchoring device configured to receive a wire lead during a surgical procedure, the anchoring device comprising:
an anchor defining a longitudinal axis and configure for insertion into an access site in a patient, wherein the anchor includes:
a first body portion; and
a second body portion movably connected to the first body portion such that the anchoring device is reconfigurable between an open configuration and a closed configuration; and
a frame connected to the anchor and configured to facilitate reconfiguration of the anchoring device between the open configuration and the closed configuration;
wherein the access site is a burr hole in a skull of a patient, wherein the first and second body portions define inner walls, wherein in the open configuration, the inner walls of the first and second body potions are separated, and in the closed configuration, the inner walls of the first and second body portions are positioned in adjacent relation such that the first and second body portions collectively define passageway configured to receive the wire lead;
wherein the anchor includes a depression in communication with the passageway and configured to receive the wire lead to inhibit excess force from being applied thereto.

16. An anchoring device configured to receive a wire lead during a surgical a procedure, the anchoring device comprising:
an anchor defining a longitudinal axis and configured for insertion into an access site in a patient, wherein the anchor includes:
a first body portion; and a second body portion movably connected to the first body portion such that the anchoring device is reconfigurable between an open configuration and a closed configuration;

a cap configured for engagement with the anchor to further secure the anchoring device within the access site;

a frame connected to the anchor and configured to facilitate reconfiguration of the anchoring device between the open configuration and the closed configuration;

wherein the cap is engaged to the anchor such that the wire lead extends through the cap.

17. The anchoring device of claim 16, wherein the frame includes:

a first frame portion connected to the first body portion; and a second frame portion connected to the second body portion.

18. The anchoring device of claim 17, wherein the first frame portion is pivotable in relation to the first body portion, and the second frame portion is pivotable in relation to the second body portion.

*    *    *    *    *